United States Patent [19]

Rice

[11] 4,236,893

[45] Dec. 2, 1980

[54] METHOD FOR THE ASSAY OF CLASSES OF ANTIGEN-SPECIFIC ANTIBODIES

[75] Inventor: Thomas K. Rice, White Bear Lake, Minn.

[73] Assignee: Minnesota Mining and Manufacturing Company, Saint Paul, Minn.

[21] Appl. No.: 28,348

[22] Filed: Apr. 9, 1979

[51] Int. Cl.³ .................... G01N 33/54; H01L 41/00
[52] U.S. Cl. .................... 23/230 B; 23/915; 310/312; 324/71 R; 422/57; 422/61; 422/69; 424/12
[58] Field of Search .................... 23/230 B; 422/61; 424/12

[56] References Cited

U.S. PATENT DOCUMENTS

| | | | |
|---|---|---|---|
| 3,720,760 | 3/1973 | Bennich | 424/12 X |
| 3,966,898 | 6/1976 | Sjoquist | 23/230 B X |
| 4,092,114 | 5/1978 | Buck | 23/230 B |

OTHER PUBLICATIONS

A. Shons et al., J. Biomed. Mater. Res., 6, 565–570, (1972).

*Primary Examiner*—Sidney Marantz
*Attorney, Agent, or Firm*—Cruzan Alexander; Donald M. Sell; Carolyn A. Bates

[57] ABSTRACT

A method and article for the determination of a particular subclass of antibody, e.g., IgA, IgE, IgM, etc., are disclosed. The method utilizes a piezoelectric oscillator having bound to the surface thereof an antigen specific for the antibody being determined. The antigen-coated oscillator is exposed to a solution containing an unknown amount of the antibody. After the antibody in the solution has attached to the antigen on the oscillator, the oscillator is exposed to a substance (sandwiching substance) which selectively binds to a specific subclass of the antibody being determined. The frequency of the oscillator is measured before and after exposure to the sandwiching substance. The change in frequency is related to the amount of the subclass of antibody bound to the oscillator, and the amount of the subclass of antibody in the solution can be quantified by reference to a standard curve.

19 Claims, No Drawings

METHOD FOR THE ASSAY OF CLASSES OF ANTIGEN-SPECIFIC ANTIBODIES

This invention relates to a method and article for the determination and quantitation of a particular species, class or subclass of antibody that reacts with a specific antigen. This method enables one to determine how much of each class of immunoglobulin in a serum [or plasma] sample is reactive with a particular antigen.

Generally, the term "antibody" refers to a protein produced by the body in response to contact of the body with a foreign substance termed an "antigen". Antibodies have the specific capacity to react with or neutralize the antigen which stimulated their production. This phenomenon is the basis of humoral aspects of the mammalian immunological system.

Antibodies to any particular antigen may be subdivided into classes. Each class is distinguishable from the others on the basis of differences in the primary sequence of amino acids that makes up that portion of the antibody molecule common to all classes of the antibody. This amino acid difference results in differences in isoelectric point, antigenicity, and behavior in vivo among the classes. In man, the classes are designated as IgG, IgM, IgA, IgD, and IgE. Examples of differences in biological properties among classes include the ability of IgE to sensitize basophils and trigger histamine release, the ability of IgG to pass across the placental membrane in contrast to IgM which cannot pass to the fetus, and the greater efficacy of IgG and IgM for interaction with serum complement as compared with the other classes. Thus, knowledge of how much of a particular class of antibody reacts with a specific antigen yields valuable information.

There are a number of instances in the practice of diagnostic clinical immunology where it is imperative to know the amount of a particular class of antibody contained in a patient's clinical sample that reacts with a given antigen. An example is the need to know the amount of IgE vs. IgG that reacts with the allergen to which an allergic patient is sensitive and/or is being treated with desensitization injections. The level of allergen-specific IgE gives a good indication of the degree of sensitivity toward the allergen while the level of allergen-specific IgG serves as an acid in monitoring the efficacy of desensitization therapy since the IgG class is thought to be protective. In the case of assaying for Rubella antibodies in pregnant women, it is imperative to know whether the antibodies found represent a fairly recent or a past infection. The determination of the antibody class, i.e., IgM vs. IgG provides this information since IgM is only associated with the initial response to the Rubella virus while IgG is indicative of past Rubella infection. There are also several types of autoimmune disease where it is desirable to know the class of antibody involved.

In the area of immunology research it is often a major part of an experiment to determine the class or subclass of an antibody being produced in order to gain a fuller knowledge of how an antibody-producing organism is reacting to exposure to the foreign antigenic material and how the organism will react to subsequent exposures.

Prior to the present invention there existed several methods of antibody class determination employed by the diagnostic and/or research worker. Fundamental to these assays is the basic concept of using a second or sandwiching layer of material specific for the particular type of antibody bound to its specific antigen. These methods however suffered from a number of disadvantages. For example, radioimmunoassays (RIAs) are generally used to assay for the classes of antibodies but they have several drawbacks. RIAs require that antibodies to the various immunoglobulin classes be tagged with a radiolabel. Consequently, these reagents are very expensive, and their handling, storage and disposal are hazardous. Preparation and use of radiolabeled reagents requires special licensing and the attention of specially trained personnel. These reagents are labile and their use requires highly sophisticated instrumentation. Furthermore, RIAs necessitate extensive calculations for analysis.

An alternative approach to RIAs has been the use of fluorescent-labeled antibodies to the specified immunoglobulin classes under study. Here again one must have specially tagged and purified immunoreagents. These fluorescent-based methods suffer from problems such as autofluorescence or quenching. In addition, the fluorescent label often makes the antibody more hydrophobic and thus prone to nonspecific binding. The results are generally of a qualitative as opposed to a quantitative nature, and their interpretation is somewhat subjective.

Another type of assay for studying the class of antigen-specific antibody in a sample is termed ELISA (Enzyme-Linked-Immuno-Sorbent-Assay). In this method antibodies to a particular type of antigen-specific antibody are linked to an enzyme, cf. U.S. Pat. No. 3,654,090. Like the other methods mentioned above, this method requires the labeling of the reagent with another molecule which can adversely affect the performance of the labelled reagent. The ELISA method also suffers from a time-dependency factor in that the incubation of all the samples being assayed must be stopped after the same time interval. Another disadvantage of the ELISA method is that often the colored products formed which serve to indicate the extent of the immunological reaction are unstable.

Immunoelectrophoresis of antisera against an antigen allows one to get some idea of the class of antibody that reacts with that antigen. However, the results are not readily quantitated.

The present invention overcomes many of the shortcomings of prior art methods for determining antibody classes. The present method uses unlabeled and unmodified antibody preparations or other specific binding reagents such as the bacterium *Staphlococcus aureus* or other cells which have surface receptors for certain types of immunoglobulins; protein A, the surface receptor of *Staphlococcus aureus* or other cell-derived molecules or receptors for specific classes of immunoglobulins; or lectins, plant products specific for certain carbohydrates as are found on different classes of antibodies. These reagents are stable, inexpensive and safe to handle.

Relatively inexpensive and unsophisticated instrumentation is required for the practice of the invention. A major advantage of the present invention is that both the total amount of antibody in a sample specific for a particular antigen and the amount of a particular class of that antibody can be determined in the same assay. Prior art methods do not readily allow for both of these determinations in the same assay. The method results in rapid, accurate and objective measurements (quantitative as wall as qualitative) of antibody classes.

The essence of the invention is the use of a piezoelectric oscillator to detect types and amounts of specific classes of antibody reactive to a particular antigen when the latter is adsorbed on the surface of the oscillator. The binding of an antibody to the surface of a piezoelectric oscillator, e.g., quartz crystal, which has adsorbed on its surface a layer of antigen specific for the antibody is known and has been used as a direct gravimetric assay for the amount of antibody in a liquid sample: (Shons et al, J. Biomed. Mater. Res. 6, 565–570 (1972)) and as an indirect competitive binding assay for the amount of antigen in a liquid sample. (Copending application Ser. No. 851,491, filed Nov. 14, 1977 in the name of Oliveira et al and assigned to the same assignee as the present invention.) What is surprising about this invention is the discovery that after a primary layer of antibody has bound specifically to an antigen adsorbed on a crystal oscillator, a second layer of antibody specific reagent can be bound to the primary layer for purposes of assaying the primary layer both qualitatively and quantitatively.

Piezoelectric oscillators are commonly used in electronic equipment or clocks as frequency standards and controllers. Generally, they consist of a small quartz wafer (or other material), having metal electrodes deposited on either side and some means provided for making electrical contact with an oscillator circuit. When placed in such a circuit, the portion of the wafer located between the electrodes vibrates with the precise natural frequency of the wafer. A given mass coupled to the electrode of the oscillator or crystal (used interchangeably herein) causes a decrease in the initial frequency of the crystal in an amount proportional to the mass added. Shons et al supra describe a direct method for measuring the amount of an antibody in a liquid sample using a piezoelectric quartz crystal. The crystal is first coated with the antigen specific for the antibody being assayed and its frequency measured. The coated crystal is then exposed to the sample containing the antibody. The change in frequency of the crystal due to antibody pickup is a direct measurement of the amount of total antibody in the sample.

An indirect method for determining the amount of an antigen in a liquid sample is disclosed by Oliveira et al supra. Piezoelectric oscillator having an antigen adsorbed on the surface thereof is exposed to a sample containing the antigen, and a predetermined amount of antibody specific for the antigen. The antigen attached to the crystal competes with the antigen in the sample for the supply of antibody. The change in frequency of the piezoelectric oscillator is compared to a reference curve, and the amount of antigen in the sample is indirectly determined.

The present invention goes beyond the assays described by Oliveria et al and Shons et al and provides a method for identifying which class of antibody has been picked up by the antigen-precoated piezoelectric oscillator.

Thus, the basis for the present invention is the employment of a piezoelectric oscillator in such a manner that after an antigen has been bound to the oscillator surface and the oscillator reacted with an antiserum to determine the total antigen-specific antibody content of that antiserum, one then applies a second layer of reactive material to the oscillator. This reactive material or "sandwiching" layer is specifically reactive with the class or subclass of antibody that was first bound to the antigen on the oscillator surface. This second or sandwiching layer has specificity for the type of antibody to be quantitated. The class of antibody bound to the antigen is determined by the specificity of the sandwiching layer toward a particular antibody class or subclass. The amount of that antibody class or subclass is determined by comparison with a standard curve.

According to the present invention there is provided a quantitative method for determining classes of antigen-specific antibodies comprising the steps of (1) contacting a liquid sample suspected of containing a preselected antibody with the surface of a piezoelectric oscillator having a layer of a antigen adsorbed thereon for which said antibody is specific; (2) washing and drying said oscillator; (3) measuring the frequency of said oscillator; (4) contacting said oscillator with liquid reagent containing a predetermined amount of a material reactive with a particular class of said antibody; (5) washing and drying said oscillator, and (6) measuring the change in resonance frequency (Hz) of said oscillator from said previous measurement.

The procedure for preparing the oscillators by adsorbing the antigen thereon prior to the initial step of the above-described method is described in copending application Ser. No. 851,491, filed Nov. 14, 1977, which disclosure is incorporated herein by reference.

Basically, the antigen may be attached to the oscillator by a number of conventional techniques known in the art for attaching proteins to solid supports. The antigen may simply be allowed to adsorb from an aqueous solution onto the surface of the oscillator. This method is least preferred because it results in a relatively high degree of nonspecific adsorption during the assay, and sensitivity is reduced.

Another technique for depositing the antigen on the oscillator is by crosslinking the protein antigen with a conventional agent such as glutaraldehyde.

Antigens may also be bound to the oscillator by first applying a priming coat. Antigens may be deposited on hydrophobic polymer-coated oscillators (such as polystyrene or fluorinated polymers) in which case attachment occurs by dispersion force interaction. One disadvantage with this method is that it may lead to nonspecific adsorption when the surface is exposed to additional proteins, for example, during the assay.

Similarly, priming materials such as gum arabic which binds proteins through anionic interactions may be used.

An especially preferred class of priming agents for the attachment of the antigen to the oscillator is described in copending application Ser. No. 851,492, filed Nov. 14, 1977, assigned to the assignee of the present application and also incorporated herein by reference. These priming agents are polymers, preferably poly(2-hydroxy-3-dimethylamino-1,4-butane) which when applied to the surface of the oscillator promote the deposition of a uniform layer of antigen on the oscillator. Nonspecific adsorption during the assay is minimized and a high degree of sensitivity is achieved.

The antigen is immobilized or adsorbed on the oscillator (treated or untreated) by exposing the oscillator to an aqueous solution of the antigen. A simple antigen may be present in the solution or the antigen may consist of a complex mixture of molecules. Optimum concentration for attachment (or adsorption) varies from antigen to antigen according to their solubility or molecular weight, however, concentrations in the range of 0.1 to 100 milligrams per milliliter are generally preferred. Attachment is accomplished preferably at room temperature and at a pH which maintains the biological activity of the antigen. Optimum time for the attachment of antigens to the oscillator varies with the molecular weight and polarity of the antigen.

Before removing the oscillator from the antigen solution, a water wash is directed into the solution and the oscillator is thoroughly washed without contacting the air. This wash procedure prevents contact of the oscillator with denatured protein at an air-protein solution interface. The oscillator is removed and allowed to dry. The frequency of the coated oscillator is then determined. The oscillator is ready to be used in an immunochemical assay.

The antigen-coated oscillator is stable and may be stored for extended periods of time (e.g. several months) without loss of immunological activity.

To assay for the amount of antigen-specific antibody in a solution, the solution is applied to the antigen-coated crystal surface. This may be accomplished either by immersion of the crystal in the antibody solution or by application of the antibody solution to a single side of a crystal. If a single side of an oscillator is used the other side may be separately employed for a subsequent assay. This solution optimally contains antibody to the specific antigen in concentrations of 0.1 to 100 ug/ml. The crystal may be incubated at temperatures preferably between 4° and 37° C. and for a period preferably ranging from 15 minutes to 24 hours.

After the oscillator is washed and dried, its resonance frequency is measured. If one desires to quantify the amount of total antibody picked up by the oscillator, it is also necessary to measure the resonance frequency of the oscillator immediately prior to contacting the oscillator with the antibody solution and compare to a standard cure.

To perform an assay for the determination and/or quantitation of the particular type of antibody bound in the first reaction, a solution of material specific for a select type of antibody is applied to the crystal surface in the manner and under the circumstances described above for the assay of the total amount of antigen-specific antibody. In this case the material used to characterize an antibody may be any material that binds specifically to a particular species, class or subclass of antibody. Such materials include anti-antibodies, Protein A, *Staphlococcus aureus* and certain lectins. Such materials must be presented to the crystal at a concentration that is in excess of that which can be bound by a crystal saturated with the first antibody.

After incubation with this antibody-specific material the oscillator is washed and dried and its resonance frequency is measured. From this reading and the past frequency a change in reading due to the added mass of the newly attached antibody-specific material is calculated. This resultant change in resonance frequency (Hz) may be interpreted in any of a number of ways. Firstly, it may be taken as a qualitative indication that the antibody bound in the primary assay was of a specific type. Secondly, by comparison to assays run with predetermined amounts of a given type of antigen specific antibody, the actual amount of antibody bound may be ascertained in ug/ml. Depending on the manner of the definition of this standardized reagent, the primary layer of antigen specific antibody may be quantitated in either units of ug/ml, IU/ml or reciprocals of dilution, i.e., titer. Alternatively, this procedure may be employed to yield data that is of value entirely on the basis of comparison of one test sample with another.

A convenient means for carrying out the method of the invention is to provide an immunological diagnostic kit comprising a piezoelectric oscillator having an antigen adsorbed thereon. In conjunction with the antigen oscillator composite there is provided a reagent containing a predetermined amount of a reagent specifically reactive with a particular class of antibody. A sample of patient serum is contacted with the oscillator. The change in frequency of the oscillator is optionally measured at this point if total antibody pick up is to be determined. After washing and drying of the oscillator, it is then contacted with the reagent containing the sandwiching material. Following incubation (preferably about 75 minutes) the oscillator is washed, dried, and its resonance frequency measured.

The change in frequency due to the attachment of the sandwiching material is directly proportional to the amount of the specific class of antibody in the serum sample.

Classes of antibodies to virtually all antigenic materials of clinical interest may be determined using the present invention. Those of particular interest include antibodies to allergens such as honey bee venom; antibodies to viral antigens; antibodies to autoantigens, i.e., to nucleic acids, to gamma globulins, to hormones or to tissue specific antigens; antibodies specific to bacterial antigens or bacterial products such as toxins and antibodies to fungal or parasitic antigens or products of these organisms.

The invention may be further described by the following non-limiting examples.

EXAMPLE 1

Assay of Human IgG and IgE Antibodies Against Honey Bee Venom

The procedure followed for this sandwich assay begins with the cleaning of the quartz crystal oscillators. The crystals are cleaned either by immersion in a 10% aqueous solution of trisodium phosphate for 1 hour at 20° C. with subsequent rinsing in distilled water or by immersion in trichloroethylene for 30 seconds followed by 5 consecutive rinses of 5 seconds each in distilled water then immersion in an ultrasonic bath containing 190 proof ethanol for 15 to 45 minutes and drying under a stream of dry nitrogen gas. The crystals were then treated with the primer poly(2-hydroxy-3-dimethylamino-1,4 butane) (DIMA) by immersion in an 0.08% aqueous solution thereof for 18 hours at 20° C. Following rinsing with distilled water, the crystals were dried. Subsequently these quartz crystal oscillators were immersed in a solution of honey bee venom (HBV, Sigma Chemical Company, St. Louis, Missouri) at a concentration of 10 mg/ml in 0.02 M phosphate buffer, pH 7.0. Adsorption of the HBV occurred during a four hour incubation at 20° C. The crystals were then rinsed with distilled water, dried and their resonance frequency measured. The assay was performed by applying 50 µl aliquots of a dilution of serum of a patient who had been undergoing desensitization therapy employing injections of honey bee venom. The serum was applied to one side of a crystal held in a horizontal position. The crystals and serum were incubated for 75 minutes at 20° C. The crystals were rinsed, dried and the resonance frequency measured.

To determine the amount of IgG of antibody bound to the honey bee venom, a second layer of antibody specific for human IgG class antibody was applied to the crystal surface. This reagent was goat anti-human IgG (Meloy Laboratories, Inc., Springfield, Virginia) applied at a concentration of 50 g/ml in 0.02 M phosphate buffered saline, pH 7.0. This was applied in a 50 μl drop to the surface of a horizontal crystal. The crystals covered with this reagent were then incubated at 20° C. for 75 minutes, rinsed, dried and their resonance frequencies noted. To determine the relative amount of anti-HBV of the IgE class that was in the serum sample, the same procedure was followed as described for IgG determination except the sandwiching layer was Sheep anti-human IgE (Pharmacia AB, Uppsala Sweden).

This same serum sample was also assayed via an RIA method to determine the concentration of IgG antiphospholipase A antibody in μg/ml. (Phospholipase A is the major allergenic component of honey bee venon.) The results of these assays are tabulated below in Table I. The change in frequency of the quartz oscillator is referred to as Hz. Shown are the Hz frequency shifts from both the primary assay for total anti-HBV antiserum and from the secondary assay for either human IgG or human IgE class antibodies as determined by the sandwich assay. These results demonstrate that the sandwich assay method yields results in basic agreement with a convention RIA methodology.

TABLE I

| Titer (μg/ml) by RIA | Hz-Total Antibody vs. HBV | ΔHz of Anti IgG vs. Total Antibody | ΔHz of Anti IgE vs. Total Antibody |
|---|---|---|---|
| 46.5 | 454.0 | 223.0 | — |
| 23.25 | 395.0 | 182.0 | 93.5 |
| 11.6 | 305.0 | 158.0 | 57.0 |
| 5.8 | 149.0 | 163.0 | 47.0 |
| 2.9 | 76.0 | 99.0 | — |

EXAMPLE 2

Assay of Human IgG Antibodies Against Phospholipase A.

A second assay was performed using nine different sera samples from patients who had been desensitized to honey bee venom. It was expected that these patients would have high levels of IgG antibody to the injected allergens. This assay was performed in the manner and with the reagents described in Example 1. However, in this instance, the antigen adsorbed onto the crystal surface was phospholipase A (PLA) (Sigma Chemical Company, St. Louis, Mo.). The PLA was applied as a 50 μl drop to a single side of a horizontal crystal one side at a time at a concentration of 5 mg/ml in 0.02 M phosphate buffer, pH 7.0.

In order to demonstrate the usefulness of this technique for determination of the actual concentration of antiPLA IgG class antibody in μg/ml the ΔHz resulting from the assay of these sera were compared with a standard curve. The standard curve was derived from an assay of aliquots of dilutions of serum having known concentration of the IgG antibody. The equation for the linear portion from 157 ΔHz to 283 ΔHz of this curve was derived and used in calculating the concentration of PLA specific IgG in the nine unknown samples. This equation is $y = bx + m$ where $y = \Delta Hz$, $b =$ the slope, $m = y$ intercept and $x =$ the antibody concentration in μg/ml. In this case $b = 10.78$ and $m = 148.5$. Because varying dilutions of these sera were employed the calculated titer from this assay equals X times the dilution factor. The following Table 2 sets forth the results of this assay and the values of IgG class anti PLA derived from RIA for purposes of comparison. The points on the curve were plotted using the following values:

| Titer (μg/ml) | ΔHz |
|---|---|
| 25.50 | 283.0 |
| 12.75 | 218.0 |
| 6.38 | 177.0 |
| 3.19 | 157.0 |

TABLE 2

| Sera | ΔHz Anti-IgG | Dilution | X | Calculated μg/ml | RIA μg/ml |
|---|---|---|---|---|---|
| 1 | 117.5 | 1:4 | 4.2 | 16.8 | 11.7 |
| 2 | 144.5 | 1:4 | 19.3 | 77.1 | 94.0 |
| 3 | 164.0 | 1:4 | 30.2 | 120.1 | 136.0 |
| 4 | 184.0 | 1:1 | 41.5 | 41.5 | 40.8 |
| 5 | 210.0 | 1:4 | 56.3 | 225.3 | 292.0 |
| 6 | 137.0 | 1:4 | 15.1 | 60.0 | 73.6 |
| 7 | 192.8 | 1:1 | 46.3 | 46.3 | 54.6 |
| 8 | 159.8 | 1:8 | 27.8 | 222.6 | 225.0 |
| 9 | 134.0 | 1:4 | 13.7 | 13.7 | 18.2 |

This example illustrates that the sandwich assay yields useful data in terms of actual concentration of antibody in units such as μg/ml. The method can be employed for useful clinical purposes such as monitoring the efficacy of desensitization therapy. The method is equally applicable to assays of antibodies that may be directed against a single antigen or to a mixture of antigens (cf. Example 1).

EXAMPLE 3

This example illustrates the efficacy of the sandwich technique in the quantitation of different classes of specific antibodies to keyhole limpet hemocyanin in the same serum.

Antiserum was raised in rabbits to the antigen keyhole limpet hemocyanin (KLH, Lot. No. 730192, A. grade, Calbiochem-Behring Corp., San Diego, Calif.) by injecting the animals with 4 mg of alum $(Al(OH)_3)$ precipitated KLH in 1 ml of saline intravenously. The rabbits were bled 3 days post injection and serum was collected. To assay for different classes of specific antibodies to KLH with the quartz crystal oscillators, the standard procedure was used (see example 1) except for the following modifications. KLH in solution (5 mg/ml) was incubated on the crystals for 24 hours instead of 4 hours. Incubations of antisera on the crystals were carried out for 3 hours instead of 75 minutes. The antiserum used was rabbit anti-KLH and the sandwiching material was sheep anti-rabbit IgG, Fc fragment, heavy chain specific, and sheep anti-rabbit IgM, heavy chain specific (Cappel Laboratories, Inc. Cochranville, Pa.). The anti-rabbit IgG used was diluted 1/10 in 0.02 M phosphate buffered saline, pH 7.0, and the anti-rabbit IgM was undiluted. Anti-rabbit IgG and anti-rabbit IgM had been shown by immuno-electrophoresis and immunodiffusion to be monospecific. The following results were obtained.

TABLE 3

| Dilution of Anti-KLH | Hz post anti-KLH[2] | Hz post anti-IgG[3] | Hz post anti-IgM[3] |
|---|---|---|---|
| 1/5 | 557 | 504 | 358 |
| 1/10 | 424 | 447 | 325 |
| 1/20 | 298 | 464 | 314 |
| 1/40 | 138 | 397 | 208 |

TABLE 3-continued

| Dilution of Anti-KLH | Hz post anti-KLH[2] | Hz post anti-IgG[3] | Hz post anti-IgM[3] |
|---|---|---|---|
| 1/80 | 45 | 339 | 148 |

[1]Values given are the averages of duplicate crystals
[2]Values given are half the values obtained from crystals with both sides reacted with anti-KLH
[3]Values given are obtained from crystals with only one side reacted with either anti-rabbit IgG or anti-rabbit IgM.

As shown by the results in Table 3, relative amounts of IgG and IgM antibodies to KLH can be measured in the same serum. Therefore, by the use of monospecific antibodies to different classes of immunoglobulin, one can quantitate the relative amounts of different classes of antigen specific antibodies in the same serum without necessitating prior separation of the classes of antibodies.

EXAMPLE 4

This example illustrates the species-specific binding affinity of anti-human IgG for human IgG in the sandwich assay.

Honey bee venom (HBV) was used as the test antigen (see example 1). Human serum with a high titer of anti-HBV activity was reacted with the crystals having HBV adsorbed thereon. Goat anti-human IgG (A102, 89373, 3.9 mg antibody/ml, Meloy Laboratories Inc., Springfield, Va.) and sheep anti-rabbit IgG were used undiluted as sandwiching layers. The following results were obtained.

TABLE 4

| Antiserum | $\Delta$Hz |
|---|---|
| Goat Anti-human IgG | 278 |
| Sheep anti-rabbit IgG | no mass added |

Therefore, when the crystals have human anti-HBV IgG on them, only goat anti-human IgG was able to bind to the crystals. It is concluded from this that the sandwich technique can be used to determine the specific species of the first layer of antibody by the use of an appropriate second layer of anti-antibody.

EXAMPLE 5

This example illustrates that when a given class or species of antibody is not detected by the corresponding anti-antibody, the same surface of the crystal can be used to assay for a different class or species of antibody by the sandwich assay.

Crystals having KLH adsorbed thereon to which was bound a layer of rabbit anti-KLH were incubated with sheep anti-rabbit IgM diluted 1/20. When no binding of the anti-IgM was measured, the same surface of the crystals were incubated with sheep anti-rabbit IgG diluted 1/20. The following results were obtained.

TABLE 5

| Antiserum | $\Delta$Hz |
|---|---|
| Anti-rabbit IgM | no mass added |
| Anti-rabbit IgG | 106 |

Therefore, when the sandwich assay has been performed to determine if a given class or species of antibody has bound to an antigen on a crystal surface and the results are negative, this procedure may be repeated on the same crystal surface using a secondary anti-antibody to a different class or species of antibody.

EXAMPLE 6

This example illustrates the use of the sandwich assay with anti-viral antibodies against viral antigens.

In order to demonstrate the applicability of this assay method to other types of antigens, the sandwich assay was applied to rabbit anti-Rubella antibodies that had reacted with Rubella virus antigens adsorbed onto quartz crystals. This assay was performed according to the method of example 1. In this case the antigens were either Rubella hemagglutination antigen or Rubella complement fixation antigen, or the appropriate controls. These are all products of Flow Laboratories, Inc. of Rockville, Maryland, and were used without modification. The first layer antisera used was either Rubella neutralizing rabbit antiserum or rabbit preserum, also from Flow Laboratories. The second layer antiserum used was sheep anti-rabbit IgG from Cappel Laboratories, Cochranville, Pa. The results are shown in Table 6.

TABLE 6

| ANTIGEN | ANTISERUM | $\Delta$Hz of RABBIT ANTIBODY | $\Delta$Hz of Anti Rabbit IgG |
|---|---|---|---|
| Hemagglutination | Neutralizing | 64 | 191 |
| Hemagglutination | preserum | 27 | 78 |
| Hemagglutination control | Neutralizing | 1 | 82 |
| Complement fixation | Neutralizing | 40 | 221 |
| Complement fixation | Preserum | No Mass Added | 72 |
| Complement fixation control | Neutralizing | 19 | 104 |

These data indicate that the sandwich assay is applicable to the characterization of antibodies directed against various types of viral antigens. The parallelism between the primary and secondary (sandwich antibody) layers points to the usefulness of this technique in characterizing anti-viral antibodies and in serving as an amplification of the initial antigen-antibody reaction.

In view of the ability to assay antibodies against a viral antigen and the ability of this procedure to quantitate the relative amounts of each class of antibody, the present invention can be used to assay for the class of anti-Rubella virus antibody present in a patient's serum. This is useful in diagnosing the occurance of Rubella infections in pregnant women.

EXAMPLE 7

This example illustrates the use of an appropriate secondary layer other than an immunoglobulin to obtain information regarding the first layer of antibodies in the sandwich assay.

Protein A synthesized by the bacteria *Staphylococcus aureus* has been shown to bind the Fc region of IgG from several species of animals. Protein A, (Sigma Chemical Co., St. Louis, Mo.) at a concentration of 5 mg/ml in 0.2 M phosphate buffered saline, pH 7.0, was incubated with crystals that had varying amounts of rabbit anti-KLH bound to the KLH on their surfaces. The following results were obtained.

TABLE 7

| Dilution of anti-KLH | $\Delta$Hz post anti-KLH | $\Delta$Hz post Protein A |
|---|---|---|
| 1/10 | 437 | 216 |
| 1/20 | 368 | 202 |

TABLE 7-continued

| Dilution of anti-KLH | ΔHz post anti-KLH | ΔHz post Protein A |
|---|---|---|
| 1/40 | 301 | 183 |
| 1/80 | 176 | 114 |

Protein A is therefore capable of binding specifically to the rabbit IgG anti-KLH on the crystals. Thus, it is possible to use other biospecific molecules that will bind to the first layer of antibodies in the sandwich assay.

EXAMPLE 8

This example illustrates the use of bacterial cells with specific surface receptors as a second sandwich layer.

Cells with receptors on their surface specific for a particular type of antibody can also be used as a sandwich layer. This layer may serve for either a qualitative or quantitative analysis of the amount and/or type of antibody bound to an antigen. In this example the crystals were prepared and assayed as described in Example 1. The antigen was bovine serum albumin (BSA). (Sigma Chemical Co., St. Louis, Mo. at 10 mg/ml in phosphate buffer pH 7.0). The primary anti-serum was Rabbit anti-BSA. The second or sandwich layer was a 10% suspension of *Staphlococcus aureus*, Cowan I, ATCC 12578, grown up in $CCY_I$ media, killed, washed and suspended in PBS. This preparation was incubated on a crystal for 75 minutes at 20° C. Table 8 gives the results of this experiment.

TABLE 8

| ΔHz with Rabbit anti-BSA | ΔHz with 10% *Staphlococcus Aureus* |
|---|---|
| 604 | 242 |
| PBS | No Mass Added |

In this case these cells have protein A on their surface. This is a molecule that binds specifically to the Fc portion of the IgG antibodies of several species.

EXAMPLE 9

This example illustrates priming of the quartz crystals with polystyrene prior to deposition of the antigen coat. Proteins bind to polystyrene through dispersion forces. To demonstrate this, crystals were dipped in 1.5% polystyrene in toluene, dried with nitrogen and kept at room temperature for 24 hours to allow residual toluene to evaporate. Phospholipase A (PLA, Sigma Chemical Co. St. Louis, Mo.) an antigenic component of honey bee venon was applied at 5 mg/ml in 0.02 M phosphate buffer pH 70. The assay was performed as described in Example 1 using as the antibody source the same type of human sera samples and antihuman IgG (Meloy, Springfield, Va.) at 50 μg/ml in 0.02 M phosphate buffered saline pH 7.0.) The frequency change (ΔHz) shown in Table 9 is a quantitation of phospholipase A specific-antibody of the IgG class.

TABLE 9

| Sera # | Titer (μg/ml) by RIA[1] | ΔHz total antibody vs. PLA | ΔHz anti IgG vs. total antibody |
|---|---|---|---|
| 1 | 3.5 | 91.5 | 93.5 |
| 2 | 31.0 | 106.0 | 160.0 |
| 3 | 41.0 | 149.5 | 184.5 |
| 4 | 51.0 | 160.5 | 183.0 |

[1]RIA (radioimmuno assay).

The data presented in Table 9 illustrate that antigen specific IgG quantitation using the sandwich assay correlates with RIA titers using polystyrene primed crystals.

EXAMPLE 10

This example illustrates that an antigen can be bound to a quartz crystal by chemical crosslinking. As an illustration, glutaraldehyde was used to crosslink the antigen. The following mixture was painted on a cleaned crystal:

100 μl of acetate buffer pH 5.0
200 μl of the antigen, phospholipase A at 10 mg/ml in 0.02 M phosphate buffer pH 7.0
50 μl of 25% glutaraldehyde in water.

To facilitate crosslinking of the antigen, the crystals were incubated at room temperature in a moist environment for 16 hours, and rinsed by immersion into distilled water 3 times for 1 hour. A non-antigenic protein was applied to react with free glutaraldehyde remaining on the crystal. To this purpose, bovine serum albumin (Sigma Chemical Co., St. Louis, Mo.) was applied at 10 mg/ml in 0.02 M phosphate buffer, pH 7.0.

The antibody assays were performed using the method described in Example 1 and the materials described in Example 9.

TABLE 10

| Sera | Titer (μg/ml) by RIA | ΔHz total antibody vs. PLA | ΔHz anti IgG vs. total antibody |
|---|---|---|---|
| 1 | 3.5 | 77.5 | 29.5 |
| 2 | 6.5 | 32.5 | 87.0 |
| 3 | 41.0 | 77.5 | 135.5 |
| 4 | 57.0 | 59.0 | 156.0 |

The data presented in Table 10 illustrate that the sandwich assay can be carried out using crosslinked antigen. Although the total antibody binding (ΔHz) to phospholipase A appears to be non-specific, the sandwich assay data (ΔHz of anti-IgG) correlated well with RIA titers.

EXAMPLE 11

This example illustrates the use of gum arabic to attach the antigen to the crystal through anionic interactions. Gum arabic (Sigma Chemical Co., St. Louis, Mo.) was applied to a crystal at 10 mg/ml in 0.02 M phosphate buffer, pH 7.2. The methodology and materials used in this assay are described in Examples 1 and 9, respectively.

The data presented in Table 11 illustrate that the sandwich assay can be used to characterize primary antibody layers that have bound to the antigen attached to gum arabic-primed crystals.

TABLE 11

| Sera | Titer (μg/ml) by RIA | ΔHz total antibody vs. PLA | ΔHz anti IgG vs. total antibody |
|---|---|---|---|
| 1 | 0. | No Mass Added | 10.0 |
| 2 | 4.8 | 108.0 | 168.0 |
| 3 | 10.25 | 111.5 | 184.0 |
| 4 | 12.75 | 115.0 | 223.0 |

What is claimed is:

1. A quantitative method for determining at least one class of antigen-specific antibodies comprising the steps of:

(1) contacting a liquid sample suspected of containing an antibody with the surface of a piezoelectric oscillator having a layer of antigen for which said antibody is specific adsorbed thereon;
(2) washing and drying said oscillator;
(3) measuring the resonance frequency of said oscillator;
(4) contacting said surface of said oscillator with a liquid reagent containing a predetermined amount of a material reactive with a particular class of said antibody;
(5) washing and drying said oscillator; and
(6) measuring the change in resonance frequency of said oscillator from said first measurement.

2. The method according to claim 1 wherein said reactive material is an anti-antibody.

3. The method of claim 2 wherein said anti-antibody is selected from the group consisting of anti-IgG, anti-IgM, anti-IgE, anti-IgA and anti-IgD.

4. The method according to claim 1 wherein said reactive material is Protein A.

5. The method according to claim 1 wherein said reactive material is antibody class specific receptors or cells having said receptor on the surface thereof.

6. The method according to claim 1 wherein said oscillator is a quartz crystal.

7. The method according to claim 6 wherein said oscillator has adsorbed thereon a monolayer poly(2-hydroxy-3-dimethylamino-1,4-butane) to which is attached said antigen layer.

8. The method according to claim 6 wherein said oscillator has adsorbed thereon a layer of polystyrene to which is attached said antigen.

9. The method according to claim 6 wherein said antigen is chemically crosslinked on said oscillator.

10. The method according to claim 1 wherein said antigen is an allergen.

11. The method according to claim 1 wherein said antigen is selected from the group consisting of viral, bacterial, fungal and parasitic antigens.

12. A diagnostic test kit for the quantitative determination of at least one class of antigen-specific antibodies comprising:
a piezoelectric oscillator having a layer of antigen for which said antibody is specific adsorbed thereon; and
a reagent containing a predetermined amount of a material reactive with a particular class of said antibody.

13. The kit according to claim 12 wherein said reactive material is an anti-antibody.

14. The kit according to claim 13 wherein said anti-antibody is selected from the group consisting of anti-IgG, anti-IgE, anti-IgM, anti-IgA and anti-IgD.

15. The kit according to claim 12 wherein said reactive material is Protein A.

16. The kit according to claim 12 wherein said reactive material is antibody class specific receptors or cells having said receptor on the surface thereof.

17. The kit according to claim 12 wherein said oscillator is a quartz crystal.

18. The kit according to claim 12 further comprising at least one reference antibody preparation containing a known amount of a specific class of antibody.

19. The kit according to claim 12 wherein said oscillator has adsorbed thereon a monolayer of poly(2-hydroxy-3-dimethylamino-1,4-butane) to which is attached said antigen layer.

* * * * *